(12) United States Patent
Bogdan

(10) Patent No.: US 9,192,513 B2
(45) Date of Patent: Nov. 24, 2015

(54) EYE TREATEMENT APPARATUS

(71) Applicant: Allan J. Bogdan, Toms River, NJ (US)

(72) Inventor: Allan J. Bogdan, Toms River, NJ (US)

(*) Notice: Subject to any disclaimer, the term of this patent is extended or adjusted under 35 U.S.C. 154(b) by 200 days.

(21) Appl. No.: 13/909,144

(22) Filed: Jun. 4, 2013

(65) Prior Publication Data

US 2013/0261570 A1 Oct. 3, 2013

Related U.S. Application Data

(63) Continuation of application No. 13/193,971, filed on Jul. 29, 2011, now Pat. No. 8,486,031.

(51) Int. Cl.
| | | |
|---|---|---|
| *A61F 9/00* | (2006.01) | |
| *A61F 9/02* | (2006.01) | |
| *A61F 9/04* | (2006.01) | |
| *G02C 5/00* | (2006.01) | |
| *G02C 11/00* | (2006.01) | |
| *G02C 7/16* | (2006.01) | |
| *G02C 1/00* | (2006.01) | |
| *G02C 7/02* | (2006.01) | |

(52) U.S. Cl.
CPC .............. *A61F 9/0026* (2013.01); *A61F 9/0008* (2013.01); *G02C 5/001* (2013.01); *G02C 5/005* (2013.01); *G02C 11/00* (2013.01); *G02C 1/00* (2013.01); *G02C 7/021* (2013.01); *G02C 7/16* (2013.01)

(58) Field of Classification Search
CPC ..... A61F 9/0026; A61F 9/0008; G02C 5/005; G02C 11/00; G02C 11/02; G02C 5/001; G02C 1/00; G02C 5/003; G02C 7/021; G02C 7/16; G02C 7/165
See application file for complete search history.

(56) References Cited

U.S. PATENT DOCUMENTS

| | | | | |
|---|---|---|---|---|
| 2,276,102 | A | * 3/1942 | Schwartz | 351/86 |
| 2,320,070 | A | 5/1943 | Derham et al. | |
| 2,722,216 | A | 11/1955 | Robbins | |
| 3,446,209 | A | 5/1969 | Macha | |
| 3,910,618 | A | 10/1975 | Massenz | |
| 4,183,355 | A | * 1/1980 | Meckler | 604/302 |
| 4,257,417 | A | 3/1981 | Gibilisco | |
| 4,468,103 | A | * 8/1984 | Meckler | 351/158 |
| 4,733,802 | A | 3/1988 | Sheldon | |
| 4,792,334 | A | 12/1988 | Py | |
| 5,030,214 | A | 7/1991 | Spector | |
| 5,037,406 | A | 8/1991 | Smith et al. | |
| 5,201,726 | A | 4/1993 | Kirkham | |
| 5,255,024 | A | 10/1993 | Jensen | |
| 5,368,582 | A | 11/1994 | Bertera | |
| 5,569,224 | A | * 10/1996 | Michalos | 604/300 |
| 5,588,564 | A | 12/1996 | Hutson et al. | |
| 5,832,930 | A | * 11/1998 | Martin et al. | 128/898 |

(Continued)

FOREIGN PATENT DOCUMENTS

FR 2635011 A1 * 2/1990 ............ A61M 31/00

*Primary Examiner* — Adam Marcetich

(74) *Attorney, Agent, or Firm* — Eckert Seamans Cherin & Mellott, LLC; David C. Jenkins

(57) ABSTRACT

An eye treatment apparatus having a guide device structured to guide a nozzle of an applicator to a position in front of an eye is provided. The guide device includes a guide surface and a stop. The guide surface is easily accessible. That is, the nozzle of an applicator may be moved, generally laterally, into contact with the guide surface. The nozzle may then slide over the guide surface to the stop. The stop is positioned so that the nozzle is disposed centrally in front of the eye.

18 Claims, 12 Drawing Sheets

(56) References Cited

U.S. PATENT DOCUMENTS

| | | | |
|---|---|---|---|
| 6,168,278 B1 | 1/2001 | Mukai | |
| 7,192,133 B1 * | 3/2007 | Yang | 351/44 |
| D614,303 S | 4/2010 | Gausmann et al. | |
| D617,443 S | 6/2010 | Grenon et al. | |
| 7,828,428 B1 * | 11/2010 | Livingston | 351/61 |
| 2008/0119800 A1 * | 5/2008 | Goldman et al. | 604/303 |
| 2009/0128773 A1 | 5/2009 | Wang | |
| 2009/0290119 A1 * | 11/2009 | Bartholomew | 351/114 |
| 2010/0160872 A1 * | 6/2010 | Harrison | 604/298 |

* cited by examiner

EYE TREATEMENT APPARATUS

CROSS REFERENCE TO RELATED APPLICATION

This application is a continuation application of U.S. application Ser. No. 13/193,971, filed Jul. 29, 2011, entitled "EYE TREATMENT APPARATUS."

BACKGROUND OF THE INVENTION

1. Field of the Invention

This disclosure relates to an eye treatment apparatus and, more specifically, an eye treatment apparatus having a guide surface structured to guide a nozzle of an applicator to a position in front of an eye.

2. Background Information

Many eye medications are applied directly to the eye. Commonly, medications are disposed in a liquid solution that is applied to the eye in drops. Other liquid medications may be applied to the eye as a mist or a spray. To accomplish such an application, the user must position the nozzle of the applicator in front of the eye. For eye drops, this is accomplished by tilting the head back and positioning the applicator over the eye. As used herein, "in front of" the eye includes "over" the eye.

Given the natural instinct to avoid anything, even liquids, contacting the eye, many users have difficulty positioning and applying such medications. For example, some people close the other eye, the one not receiving medication, leaving the user without a sense of depth perception during application of the medication. Some people have an aversion to anything close to their eye and, as such, hold the applicator far from the eye. Such difficulties are compounded when additional factors are added. For example, the elderly or those with various other conditions may have difficulty holding their arms steady. Further, conditions such as glaucoma, which may affect both eyes, may prevent the user from determining when the applicator is directly in front of the eye.

Attempts to provide a guide device typically provided a nozzle mount structured to accept the nozzle of a bottle or the tip of an eyedropper. The nozzle mounts included an unobstructed passage for the medication, but also included the mounting device that extended about the opening. The nozzle mounts were disposed on frames that could be mounted on the user's nose or simulated eyeglass frames. Such nozzle mounts, while effective, substantially blocked the user's view. Even when such devices were made of transparent materials, the thickness and/or curvature of the device would interfere with the passage of light to the user's eye. That is, the nozzle mount would refract or block light passing through the nozzle mount. Thus, the user would typically only wear the device when medicine was being applied; or, if the user continued to wear the device, the user's field of view was blocked or distorted.

SUMMARY OF THE INVENTION

The disclosed and claimed concept relates to an eye treatment apparatus having a guide surface structured to guide a nozzle of an applicator to a position in front of an eye. By way of example, one embodiment is similar to a pair of eyeglasses, but at least one lens has an opening positioned in front of the eye. The user positions the nozzle of the applicator in the opening, opens the eye, and applies the medication. Preferably, the opening is sized so as to not allow the entire nozzle to pass through the opening and so that the portion of the nozzle that does enter the opening does not extend substantially beyond the inner side of the lens. By way of another example, the opening may be a V-shaped cutout, and more preferably an inverted V-shaped cutout. That is, the wide, open portion of the "V" may be disposed along the lower edge of the lens and the vertex of the cutout is positioned just above a position in front of the eye. Those with limited control of their arms/hands and/or those with difficulty seeing may position the nozzle of the applicator anywhere on the edge of the cutout and then move the nozzle to the vertex to properly position the nozzle.

A further aspect of the disclosed concept is that the at least one guide device provides a substantially unobstructed view. That is, unlike the prior devices that used a nozzle mount, the present concept provides for an unobstructed view through an opening. The opening does not have a mount or tubular member structured to accept a nozzle of an applicator. Instead, the nozzle of the applicator simply rests on the guide surface. Further, the object that creates the guide surface is thin, preferably less than 0.06 in. thick, when the guide is created by a planar member, or, less than 0.06 in. in diameter when the guide surface is created by a rigid member. The material, which is preferably transparent, is sufficiently thin so that light does not refract light, or otherwise cause the light entering the user's eye to become significantly distorted. Further, the rigid member, which is preferably a thin wire, is sufficiently thin that unobstructed light may enter the pupil even when the rigid member is directly in front of the pupil. That is, the rigid member has a diameter that is smaller than a user's pupil, under normal light conditions, so that at least some light may pass through the user's pupil even with the guide member directly in front of the pupil.

In this configuration, the user may wear the eye treatment apparatus without having an obstructed view. The device may further be fitted with corrective lenses and/or shaded lenses (as in sunglasses). Such lenses may be movable coupled to the frame assembly, typically in a "flip-up" configuration. Thus, for users who wear corrective lenses and/or sunglasses, the user may have the eye treatment apparatus in position at all times without having an obstructed view. To use the eye treatment apparatus, the user simply flips the movable lenses up, positions the applicator nozzle using the guide device, and applies the medication.

In another embodiment, the frame assembly may include a lens with an unobstructed aperture. The unobstructed aperture is an opening in the lens free from constructs that would block the user's view. That is, constructs such as a threaded socket or a tapered profile to the aperture may aid a user in positioning a nozzle in the aperture, but these constructs also block the user's view and/or interfere with light passing to the user's eye. An unobstructed aperture, on the other hand, is substantially invisible to the user. Preferably, the lens having the aperture is thin so as to reduce the refraction created by light passing through the lens' edge defining the aperture. As with the embodiment above, the frame assembly may include movable lenses, such as, but not limited to, flip-up shaded lenses. Further, this embodiment may include a magnetic material disposed about the unobstructed aperture. This additional element cooperates with a magnetic material disk disposed on the applicator nozzle for the medicine. At least one of the magnetic material elements must be magnetic, the other magnetic material element may be a ferrous material or another material capable of being attracted to a magnet. In the preferred embodiment, the applicator disk is the magnetic element and a thin ferrous wire or ring extends about the unobstructed aperture.

BRIEF DESCRIPTION OF THE DRAWINGS

A full understanding of the invention can be gained from the following description of the preferred embodiments when read in conjunction with the accompanying drawings in which.

DESCRIPTION OF THE PREFERRED EMBODIMENTS

As used herein, "coupled" means a link between two or more elements, whether direct or indirect, so long as a link occurs.

As used herein, "directly coupled" means that two elements are directly in contact with each other.

As used herein, "fixedly coupled" or "fixed" means that two components are coupled so as to move as one while maintaining a constant orientation relative to each other. The fixed components may, or may not, be directly coupled.

As used herein, a "substantially unobstructed view" means a view free from obstructions such as, but not limited to a socket for an applicator nozzle or tubular member in which an applicator nozzle may be placed. Such devices, even if made from transparent materials, are still noticeable by a user and cannot provide a "substantially unobstructed view."

As used herein, a "guide device" includes a structure, such as the guide surface, that provides a surface against which an application nozzle may be moved along until the applicator nozzle is in a desired final position. That is, the guide device is structured to guide the nozzle to the proper location. As such, a simple opening is not a "guide device."

As used herein, "easily accessible," and variations thereof, relate to access by an applicator nozzle. For an object, such as a guide surface, to be "easily accessible," the object must have an open space thereabout that is substantially greater than the diameter of the applicator nozzle. The open space must extend in the plane generally perpendicular to the longitudinal axis of the nozzle, thus allowing the nozzle to easily be moved laterally into contact with the guide surface. An opening in a generally planer member that is accessed axially, i.e. wherein the nozzle is moved axially, does not provide "easy access," despite the open space in front of the planar member.

As used herein, a "vertex" is point at which the sides of an angle intersect.

As used herein, "central position" or "centrally positioned" means directly in front of a user's pupil when the user is looking straight ahead.

As used herein, a "magnetic element" is either a member that is attracted to materials such as iron or steel, e.g., a typical magnet, or a member of iron or steel, or a similar material, to which a magnet is attracted.

Figure 1:
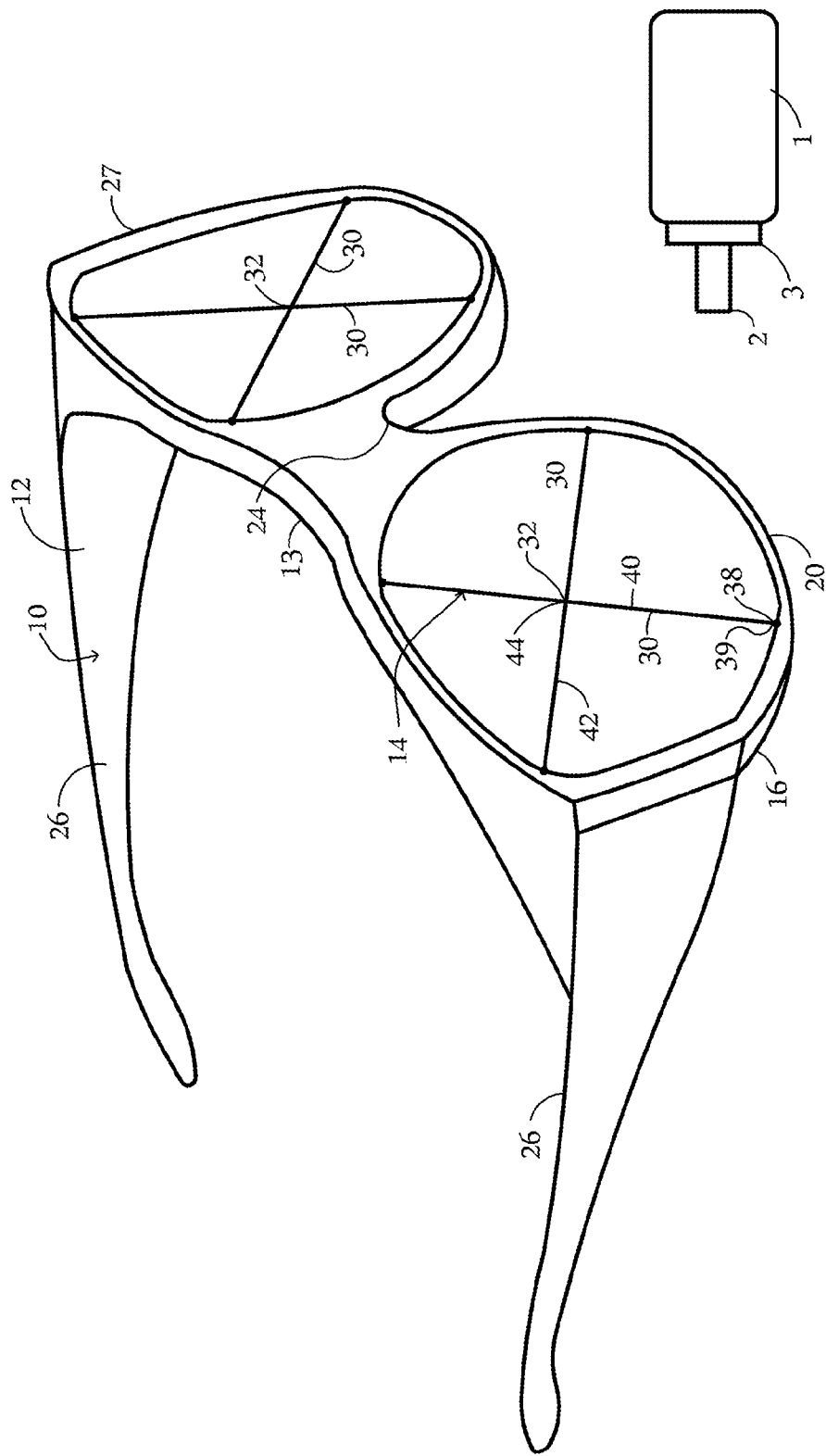
FIG. 1 is an isometric view of a frame assembly having one embodiment of the guide device.

The disclosed and claimed concept discussed below is structured to operate with applicator 1, as shown in FIG. 1. The applicator 1 is structured to dispense fluids, which are typically medicated. As used herein, "medication" means any fluid applied to the eyes. The applicator 1 has a nozzle 2 from which the fluid is dispensed. The nozzle 2 has a cross-section that is, typically, circular. The nozzle 2 is elongated and may have a radial flange 3, or other radially extending surface, that is offset from the distal tip of the nozzle 2. An "applicator" 1 includes a bottle with a built in nozzle 2 and an eyedropper (not shown).

Figure 2:
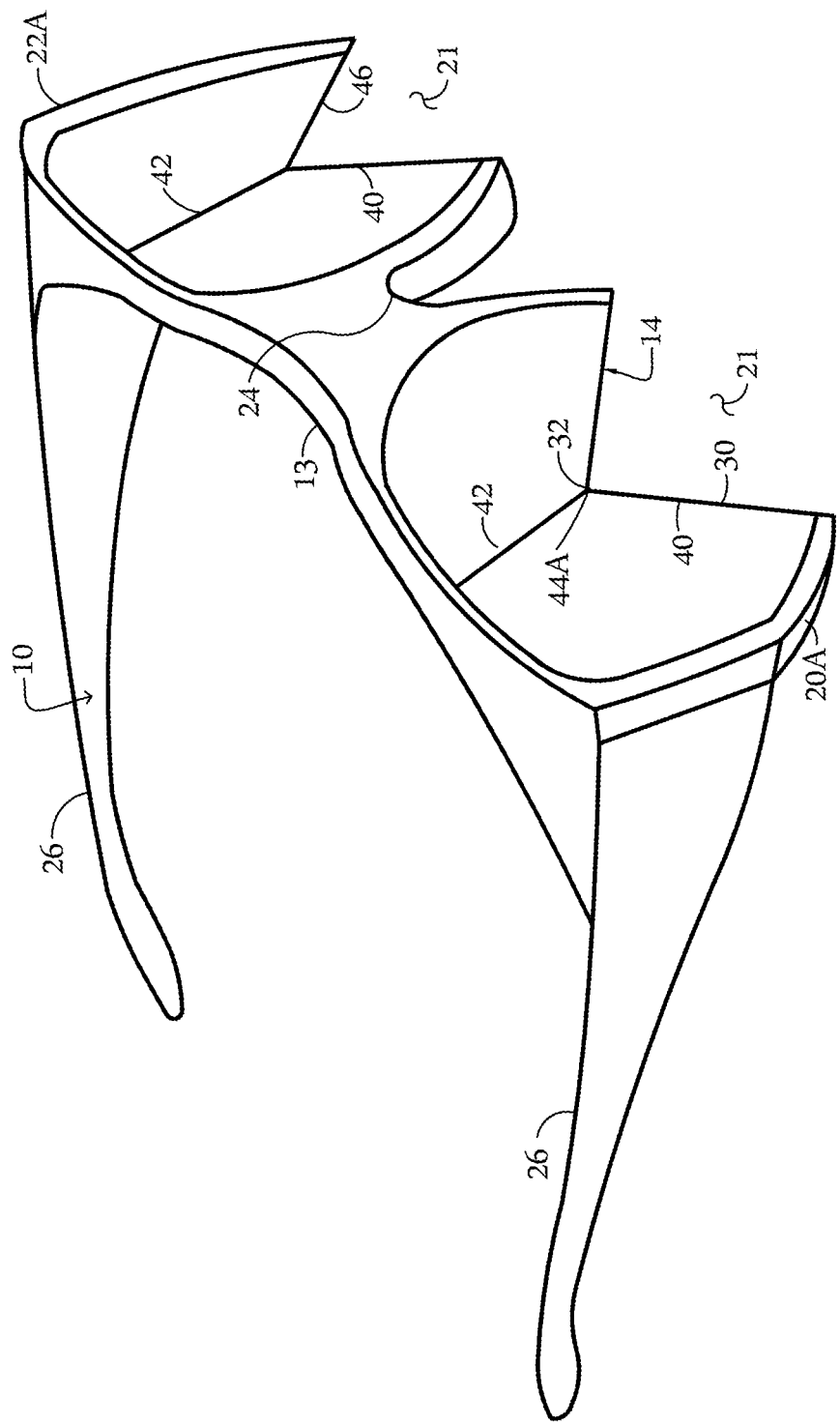
FIG. 2 is an isometric view of a frame assembly having another embodiment of the guide device.

As shown in FIG. 1, an eye treatment apparatus 10 includes a frame assembly 12 and at least one guide device 14. The frame assembly 12 has at least one frame member 16 structured to be disposed adjacent to at least one eye of the user. Preferably, the at least one frame member 16 includes at least one, and typically two, rigid loops 20, 22 or partial loops 20A, 22A (FIG. 2). The frame assembly 12 also include a bridge member 24 and two temples 26. The loops 20, 22 are structured to be disposed about the eye. The bridge member 24 is disposed between the loops 20, 22 and is structured to rest on the user's nose. One temple 26 is pivotally coupled to the outer edge of each loop 20, 22. Thus, the frame assembly 12 is similar to common eyeglass frames. The frame assembly 12, however, may have an extended top member 13. That is, the top member 13 extends in a horizontal plane. In this configuration, the forward edge of the top member 13 is horizontally spaced from the user's eye when the user wears the frame assembly 12. This distance allows for the at least one guide device 14 to be spaced from the user's eye as well.

The at least one guide device 14 is structured to be positioned in front of at least one eye. It is understood that each loop 20, 22 may, and typically does, include a guide device 14. That is, typically, the at least one guide device 14 includes two guide devices 14, one guide device structured to be positioned in front of each of the user's eyes. Such guide devices 14 are preferably substantially similar, but any of the embodiments of the guide device 14, discussed below, may be coupled to a frame assembly 12. That is, there may be two different guide devices 14 on a single frame assembly 12. The following discussion shall address a single guide device 14 for each embodiment, but it is understood that two such guide devices 14 may be coupled to the frame assembly 12.

In each embodiment, the guide device 14 has a guide surface 30 and a stop 32. The stop 32 is structured to arrest the movement of an applicator nozzle 1, as described below. The stop 32 is disposed at a fixed location and is, preferably, adjacent a central position in front of an eye when the frame assembly 12 is worn; this is because the dimensions of the nozzle 2 typically do not allow the opening within the nozzle 2 to be disposed at the stop 32. Thus, slightly offsetting the stop 32 from the central location allows the opening within the nozzle 2 to be centrally positioned in front of the eye. Alternatively, for medications that are to be applied to a selected, non-central position, e.g. the corner of the eye, the stop 32 may be positioned adjacent the selected location. The guide surface 30 provides a path, that is, a surface the nozzle 2 may be moved along until the nozzle 2 reaches the stop 32.

The guide surface 30 is easily accessible. Further, the orientation of the user's head and the eye treatment apparatus 10 is generally not relevant; if the medication is a liquid, it is understood that the user may position the nozzle 2 and then tilt the head back, or tilt the head back and then position the nozzle 2. If the medication is a spray, or of a similar nature, the user may use the eye treatment apparatus 10 with the head in an upright orientation.

In one embodiment, the guide device 14 includes at least two taut tension members 40, 42 structured to be positioned in front of at least one eye. That is, the tension members 40, 42 are coupled to the frame assembly 12 and, more specifically, to a loop 20. The tension members 40, 42 are positioned so that, when the frame assembly 12 is worn, the tension members 40, 42 are disposed in front of the eye. The at least two tension members 40, 42 form a vertex 44. The vertex 44 is the stop 32. The vertex 44 is, preferably, disposed immediately adjacent the central position in front of the eye for the reasons detailed above. The vertex 44 may, however, be offset from the central position. The tension members 40, 42 are, preferably a thread or a wire having a diameter between about 0.03 in. and 0.06 in. and more preferably about 0.045 in.

The tension members 40, 42, preferably, are disposed in a substantially similar plane and cross each other, i.e. the tension members form an "X" shape. That is, the ends of each tension member 40, 42 are coupled to the loop 20 generally opposite each other. The ends of the tension members 40, 42 may be embedded in the loop 20 or there may be a tension member mounting device 38, such as, but not limited to a lug 39 about which the tension members 40, 42 may be wrapped. Further, in a less preferred embodiment, the tension members 40, 42 may actually be a single member (not shown), rather than two separate members. In this instance, it is understood that the identified tension members 40, 42 are portions of the unitary tension member.

Figure 3:
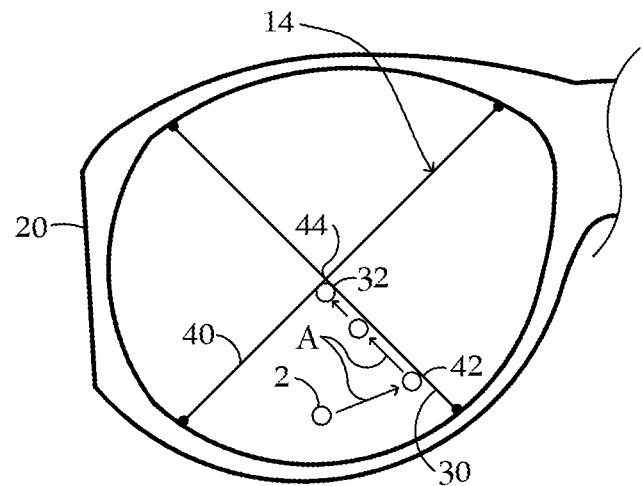
FIG. 3 is a detailed view of the embodiment in FIG. 1.

The intersection of the tension members 40, 42 is the vertex 44. The tension members 40, 42 may be disposed at a right angle to each other, but preferably there are two obtuse angles. As shown in FIG. 1, the obtuse angles face vertically and the vertex 44 is disposed slightly above the central position. In this configuration, and in use, a user would position the nozzle 2 in the space defined by the lower obtuse angle of the two tension members 40, 42 and the frame loop 20, 22. It is noted that the space between obtuse angle of the tension members 40, 42 is much larger than a nozzle 2, thus the tension members 40, 42 are easily accessible. As shown by the path A in FIG. 3, the user would then move the nozzle 2 toward one of the tension members 40, 42. Whichever of the tension members 40, 42 the nozzle 2 contacts is the guide surface 30. As further shown by path A, the user moves the nozzle 2 along the guide surface 30 until the nozzle 2 reaches the vertex 44 and the motion is arrested by the other tension member 42. Thus, the nozzle 2 is guided to the proper final location.

Figure 4:
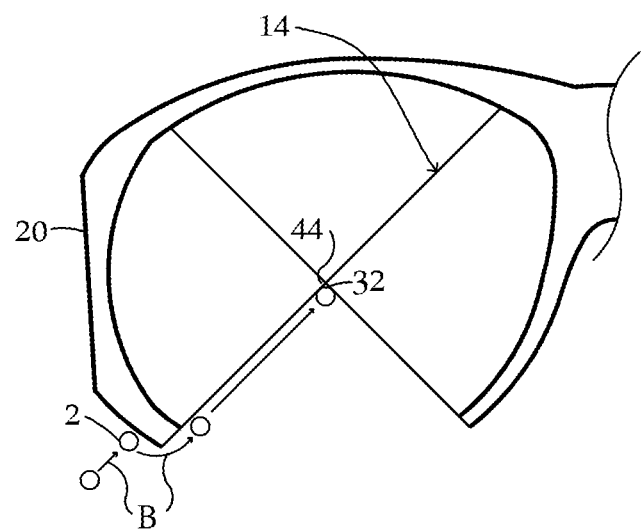
FIG. 4 is a detailed view of another embodiment of the guide device.

As noted above, the frame loops 20, 22 may be incomplete loops 20A, 22A, as shown in FIG. 2. That is, the open loop 20A includes an opening 21 in the perimeter. With the tension members 40, 42 configured as described in the paragraph above, the user may utilize the guide device 14 in a similar manner, except the user may initially position the nozzle 2 outside of the frame assembly 12. The user may, in fact, use the outer side of the frame assembly 12 as part of the guide surface 30, as shown by path B, as shown in FIG. 4. It is understood that the opening 21 in the loop 20A may be disposed at any location about the loop 20A. For example, if a user finds that it is easier to approach the eye from the side, the opening 21 in the loop 20A may be disposed on the outer vertical side of the loop 20A (not shown). Preferably, in this embodiment, the tension members 40, 42 would be configured so that the obtuse angles faced horizontally.

In another embodiment, shown in FIG. 2, the at least two tension members 40, 42 are configured as a "V." As before, the "V" preferably is an obtuse angle, and, the opening may face any direction. As shown, the "V" is inverted with the opening facing downwardly. The formation of the "V" shape may be accomplished in at least two ways. First, there may be two tension members 40, 42 wherein one tension member 40, hereinafter the "first" tension member 40 is coupled to the loop 20 at two locations generally on the same side of the loop 20, and the other tension member 42, hereinafter the "second" tension member 42, is coupled to the loop at a location generally equidistant from the ends of the first tension member 40 and on the opposite side of the loop 20. The second tension member 42 is much shorter than the first tension member. The second tension member 42 is coupled to the first tension member 40 at a medial location. As noted above, the tension members 40, 42 are drawn taut. In this configuration, the first tension member 40 is shaped as an inverted "V" having a vertex 44A. As before, the vertex 44A is the guide device stop 32. Further, the vertex 44A is, preferably, located adjacent the central position in front of the eye. Alternatively, the first tension member 40 may be split into two tension members 40, 46, as shown in the right loop 22A in FIG. 2, and all three tension members 40, 42, 46 may be joined at the vertex 44A. Preferably, the vertex 44A is structured to centrally position an applicator nozzle in front of at least one eye. The vertex 44A may, however, be offset from the central position.

In use, the user positions the nozzle 2 in the space defined by the two arms of the "V" shaped first tension member 40 (or the first and third tension members 40, 46) and the loop 20. The user moves the nozzle 2 towards one of the aims of the first tension member 40. Whichever arm of the first tension member 40 is contacted becomes the guide surface 30. The user then moves the nozzle 2 along the guide surface 30 until the nozzle 2 reaches the stop 32, which is the vertex 44A. This embodiment may also use a loop 20A having an open portion at the mouth of the "V."

Figure 5:
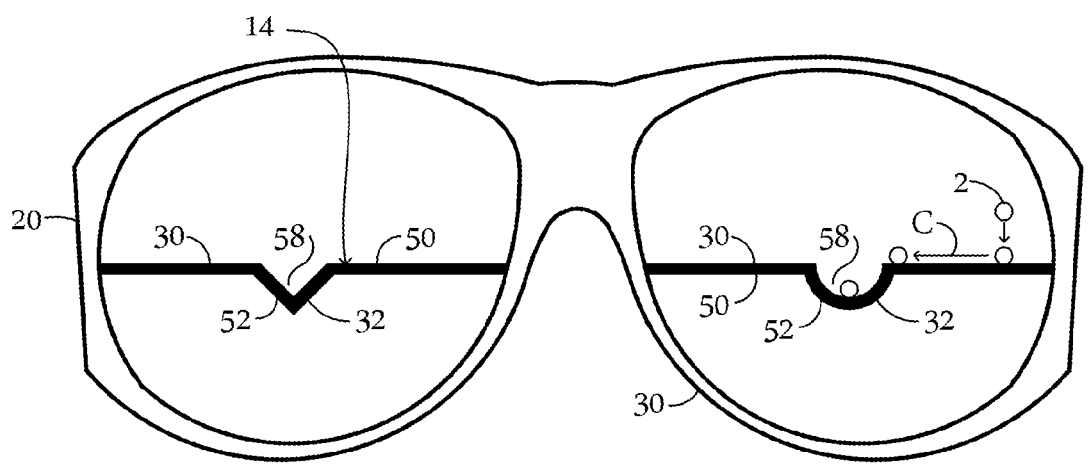
FIG. 5 is a front view of a frame assembly having another embodiment of the guide device.

In an alternate embodiment, shown in FIG. 5, the guide device 14 is formed from at least one rigid member 50. The rigid member 50 is, preferably, thin and substantially transparent. That is, the rigid members 50, preferably, have a vertical height when positioned in front of an eye looking horizontally, of between about 0.04 in. and 0.07 in., and more preferably about 0.05 in. The rigid member 50 is made, preferably, from a transparent plastic, but may be metal or a composite material as well. The rigid member 50 is coupled to the loop 20 and extends in front of the eye when the frame assembly 12 is positioned on the user's face.

In one embodiment, there is a rigid member 50 extending across the loop 20. Preferably, the member 50 extends substantially horizontally. At a central position, preferably, there is a deformation 52 that acts as the guide device stop 32. The deformation 52 is, preferably, selected from the group including a U-shaped portion 54 (right side) in the at least one rigid member 50 and a V-shaped portion 56 (left side) in the at least one rigid member 50. The U-shaped portion 54, or the V-shaped portion 56, preferably, has an upper opening 58 (assuming the "U/V" is not inverted) sized slightly larger than the nozzle 2. In this configuration, the upper surface of the rigid member 50 is the guide surface 30; if the deformation 52 is inverted, the lower surface of the rigid member 50 is the guide surface 30. It is noted that the space between the guide surface 30 and the upper portion of the loop 20 is much larger than the nozzle 2 and provides easy accessibility to the guide surface 30. Preferably, the deformation 52 is structured to centrally position an applicator nozzle in front of at least one eye. The deformation 52 may, however, be offset from the central position.

In use, and as shown by path C in FIG. 5, the user positions the nozzle in the space above the rigid member 50 and moves the nozzle into contact with the rigid member 50. The nozzle 2 is then slid over the upper surface, i.e. the guide surface 30, until the nozzle 2 moves into the deformation 52. Once in the deformation 52, the motion of the nozzle 2 is arrested and the medication may be applied.

Figure 6:
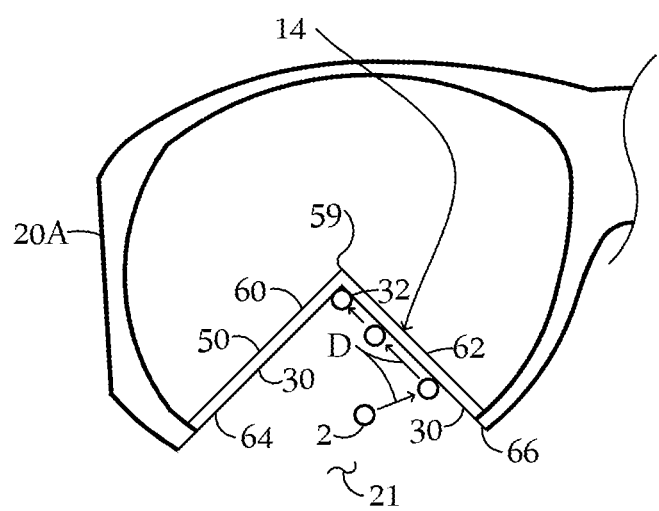
FIG. 6 is a detailed view of another embodiment of the guide device.

In another embodiment using rigid members 50, the rigid member 50 forms an inverted "V." As shown in FIG. 6, this embodiment may take advantage of a configuration similar to the open loop 20A described above. More specifically, the loop 20 is deformed so that the loop 20 is not generally circular, but instead includes the rigid member 50 that forms the inverted "V." For the sake of this discussion, however, the elements shall be identified as separate elements even though the loop 20A and the rigid member 50 may be a unitary body. Thus, the open loop 20A has an opening 21 on the lower side. The rigid member 50 is shaped as an inverted "V" having a vertex 59, two arms 60, 62, and two tips 64, 66. As before, the vertex 59 is the guide device stop 32. The rigid member tips 64, 66 are coupled to the edges of the opening 21 in the loop 20A. Preferably, the "V" formed by the rigid member 50 is an obtuse "V." It is noted that the space between the rigid member tips 64, 66 is much larger than the nozzle 2 and provides easy accessibility to either arm of the rigid member 50. Preferably, the vertex 44 is structured to centrally position an applicator nozzle 2 in front of at least one eye. The vertex 44 may, however, be offset from the central position.

In use, and as shown by path D in FIG. 6, the user positions the nozzle 2 in the space between the rigid member tips 64, 66 and moves the nozzle 2 into contact with the rigid member 50 and, more specifically, into contact with one of the rigid member arms 60, 62. The nozzle 2 is then slid over the lower surface of one of the arms 60, 62, i.e. the guide surface 30, until the nozzle 2 moves into the vertex 44. Once in the vertex 44, the motion of the nozzle 2 is arrested and the medication may be applied.

Some user's lack sufficient control over their hands to maintain a nozzle 2 in the guide device stops 32 described above. For such users, the guide device stop 32 may be formed as an aperture having a border extending over 360 degrees. There must, however, still be easy access to such a guide device stop 32. That is, it is not acceptable to move the nozzle 2 axially toward the aperture/guide device stop 32. Thus, in another embodiment utilizing rigid members 50, shown in FIG. 7, there are four rigid members 50; a first elongated member 70, a second elongated member 72, a third elongated member 74, and a fourth elongated member 76. The first and second elongated members 70, 72 being a first pair of elongated members 80 which are disposed substantially parallel to each other. The third and fourth elongated members 74, 76 are a second pair of elongated members 82 which are disposed, preferably, at a slight angle relative to each other. The first and second pairs of rigid members 80, 82 are, preferably disposed in a plane and may intersect each other. In another embodiment, the first and second pairs of rigid members 80, 82 are disposed in immediately adjacent planes. The first and second pairs of rigid members 80, 82 are substantially perpendicular to each other, thereby generally forming a crosshatch with a central opening 84. One elongated member, herein the first member 70, has a break 86 and a hinge 88. The break 86 is disposed at the intersection (which includes the point where the members are the closest to each other, if there is no contact between the members) of the third elongated member 74 and the first elongated member 70. The hinge 88 is disposed at the intersection of fourth elongated member 76 and the first elongated member 70. The segment of the first elongated member 70 between the third elongated member 74 and the fourth elongated member 76 is a "door" 89. The door 89 is hinged at one end and free at the other. In this configuration, the door 89 may move between a closed, first configuration, wherein the longitudinal axis of the door 89 is generally aligned with the longitudinal axis of the other portions of the first elongated member 70, and an open, second configuration, wherein the door 89 has pivoted about the hinge 88 and extends into the central opening 84. The hinge 88 may be a mechanical hinge but, preferably, is a "one way" living hinge structured to open into the central opening 84, and to not open away from the central opening 84. That is, if the door 89 is biased toward the central opening 84, the door moves between the first and second configurations. If the door 89 is biased away from the central opening 84, the hinge 88 does not allow the door 89 to move.

In this configuration, the gap between the second pair of elongated members 82 is much wider on one side of the opening 84 than on the other. The wide side is much wider than a nozzle 2 and provides easy accessibility to the guide surface 30. In this configuration, one of the second pair of elongated members 82 is the guide surface 30. Further, the guide device stop 32 is one of the inner edges of said crosshatch central opening 84. Preferably, the crosshatch central opening 84 is structured to centrally position an applicator nozzle in front of at least one eye. The crosshatch central opening 84 may, however, be offset from the central position.

Figure 7:
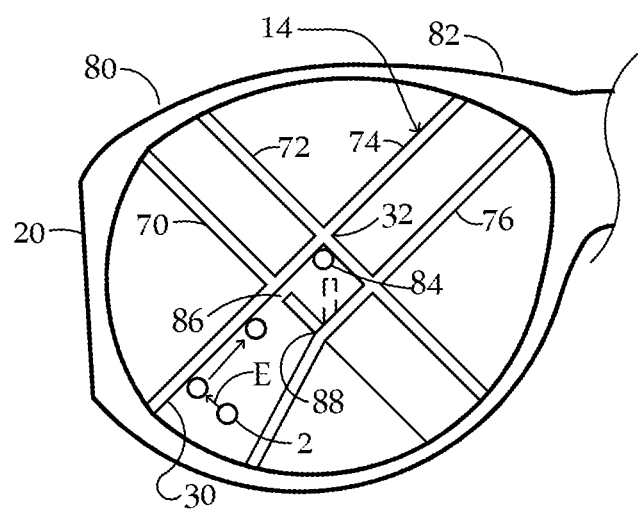
FIG. 7 is a detailed view of another embodiment of the guide device.

In use, and as shown by path E in FIG. 7, the user positions the wide portion of the gap between the second pair of elongated members 82 and moves the nozzle 2 into contact with one of the third or fourth rigid members 74, 76. The nozzle 2 is then slid over the surface of one of the third or fourth rigid members 74, 76, which becomes the guide surface 30. When the nozzle 2 reaches the door 89, the hinge 88 swings inwardly toward the opening 84, i.e. the door 89 moves into the second configuration, allowing the nozzle 2 to move into the opening 84. Preferably, once the nozzle 2 is in the opening 84, the hinge 88 returns to the first position thereby trapping the nozzle 2 in the central opening 84. Once in the central opening 84, the motion of the nozzle 2 is arrested and the medication may be applied.

Figure 8:
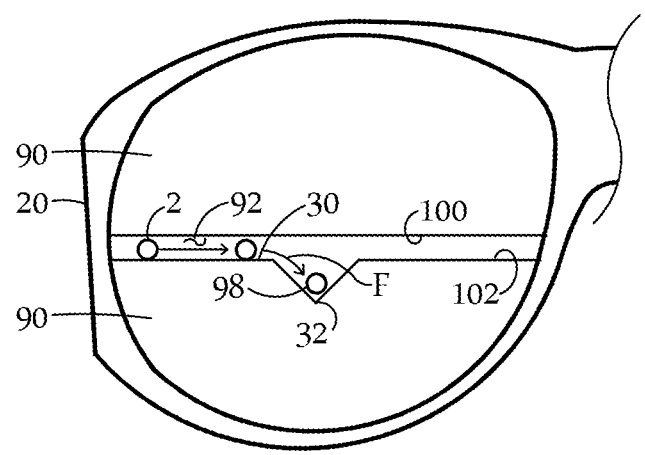
FIG. 8 is a detailed view of another embodiment of the guide device.
Figure 9:
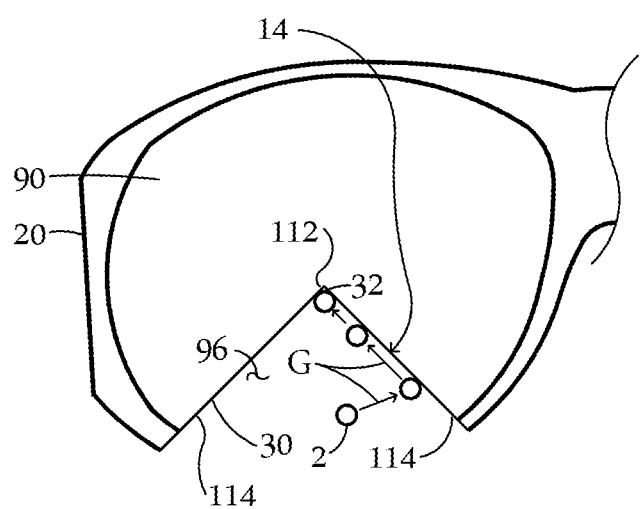
FIG. 9 is a detailed view of another embodiment of the guide device.

In another embodiment, the guide device 14 utilizes at least one transparent lens 90 structured to be positioned in front of one of the user's eyes. The at least one guide device 14 is an opening 92 in the lens 90. The opening 92 includes a guide surface 30 that extends in front of at least one eye of the user. The opening 92 may be either a slot 94 (FIG. 8) or a V-shaped cutout 96 (FIG. 9).

In the embodiment wherein the opening 92 is a slot 94, the slot 94 preferably extends horizontally in front of the user's eye. One, or both edges of the slot 94 includes a deformation 98. The deformation 98 is the guide device stop 32. Preferably, the deformation 98 is structured to centrally position an applicator nozzle 2 in front of at least one eye. The deformation 98 may, however, be offset from the central position. The lens surface 100, 102 along the slot 94 having the deformation 98 is the guide surface 30. The deformation 98 is the guide device stop 32. The slot 94 is sized so as to allow the nozzle 2 easy access to the guide surface 30. As can be seen, this embodiment is similar to the embodiment having a rigid member 50 with a deformation 52, described above. Operation of this embodiment is also similar. That is, as shown in FIG. 8 and at path F, the user inserts the nozzle 2 into the slot 94, moves the nozzle 2 into contact with the guide surface 30, and slides the nozzle 2 over the guide surface 30 until the motion is arrested by the deformation 98. At this point, the medication may be applied.

In another embodiment, the lens 90A has a V-shaped cutout 96. This is similar to the embodiment having a V-shaped rigid member 50, as described above. The frame assembly 12 may include a full loop 20 or a partial loop 20A having an opening 21 aligned with the V-shaped cutout 96. The V-shaped cutout 96 has a vertex 112 and two edges 114, 116. The vertex 112 is the guide device stop 32. The space created by the V-shaped cutout 96 is much larger than the nozzle 2, thus, there is easy access to either of the two edges 114, 116. In use, and as shown by path G on FIG. 9, the user positions the nozzle 2 in the V-shaped cutout 96, and moves the nozzle to one edge 114, 116, which becomes the guide surface 30. The user may then slide the nozzle 2 over the guide surface 30 until it reaches the guide device stop 32, that is, the vertex 44.

Figure 10:
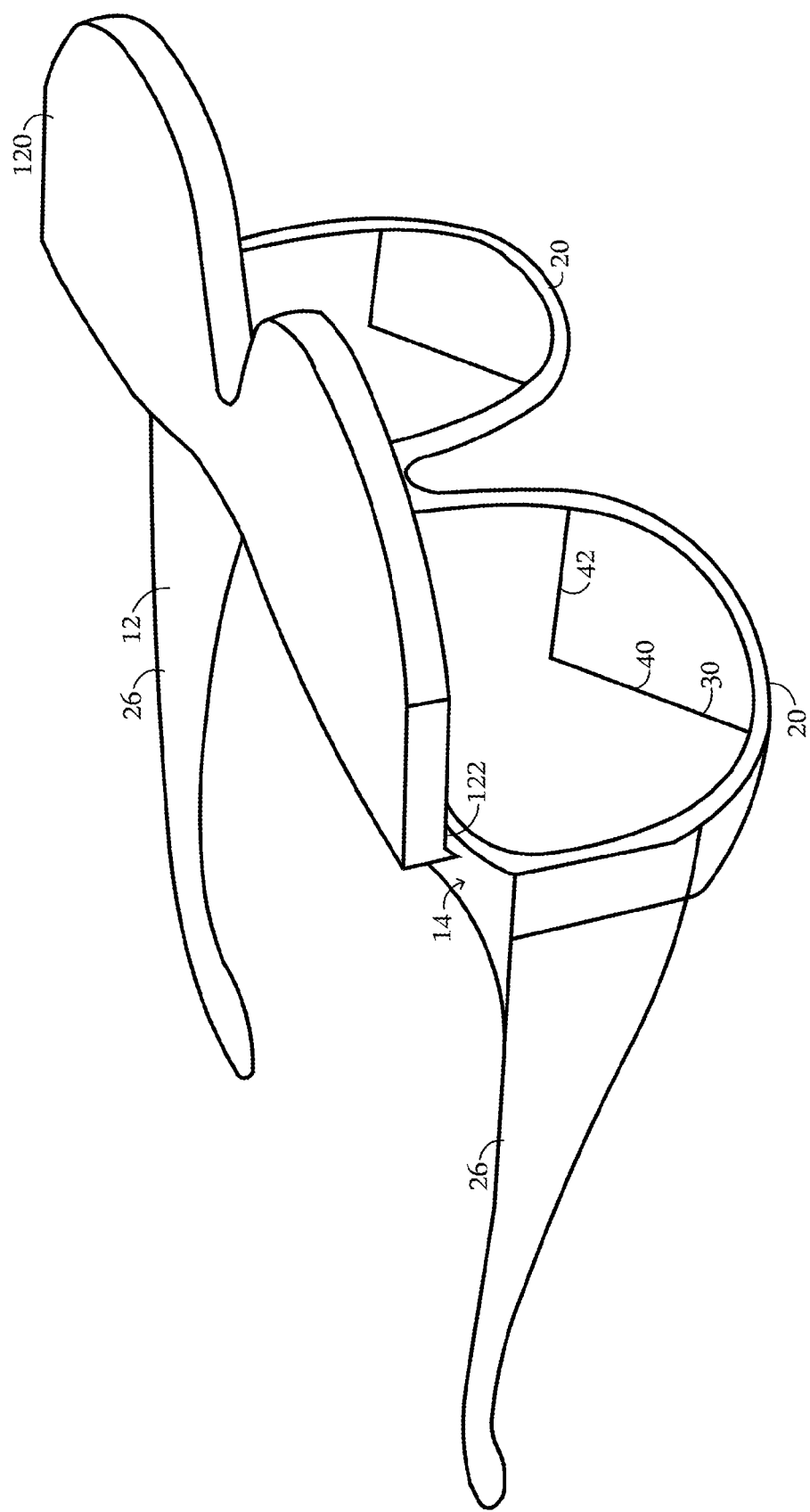
FIG. 10 is an isometric view of a frame assembly having one embodiment of the guide device and a movable lens.

Regardless of the type of guide device 14 used, the frame assembly 12 may further include at least one movable lens 120, shown in FIG. 10. The movable lens 120 is movably coupled to the frame assembly 12 and may be moved between a first position, wherein the movable lens 120 is not in front of the user's eye, and a second position, wherein the movable lens 120 is in front of the user's eye. Typically, the lens 120, or a pair of lenses, are coupled to the frame by a hinge 122 disposed along the upper side of the lenses 120. Such lenses 120 are commonly identified as "flip-up" lenses and are structured to move between the first and second positions. The at least one movable lens is selected from the group comprising: a corrective lens, a shaded lens, and a shaded corrective lens. If the lenses are shaded, preferably, the at least one guide device 14 is made from a material matching, or substantially matching, the color of the shaded lenses 120. Thus, when the lenses 120 are in the first position, the at least one guide device 14 blends in with the shaded lenses 120 and is less noticeable to the user.

Figure 11:
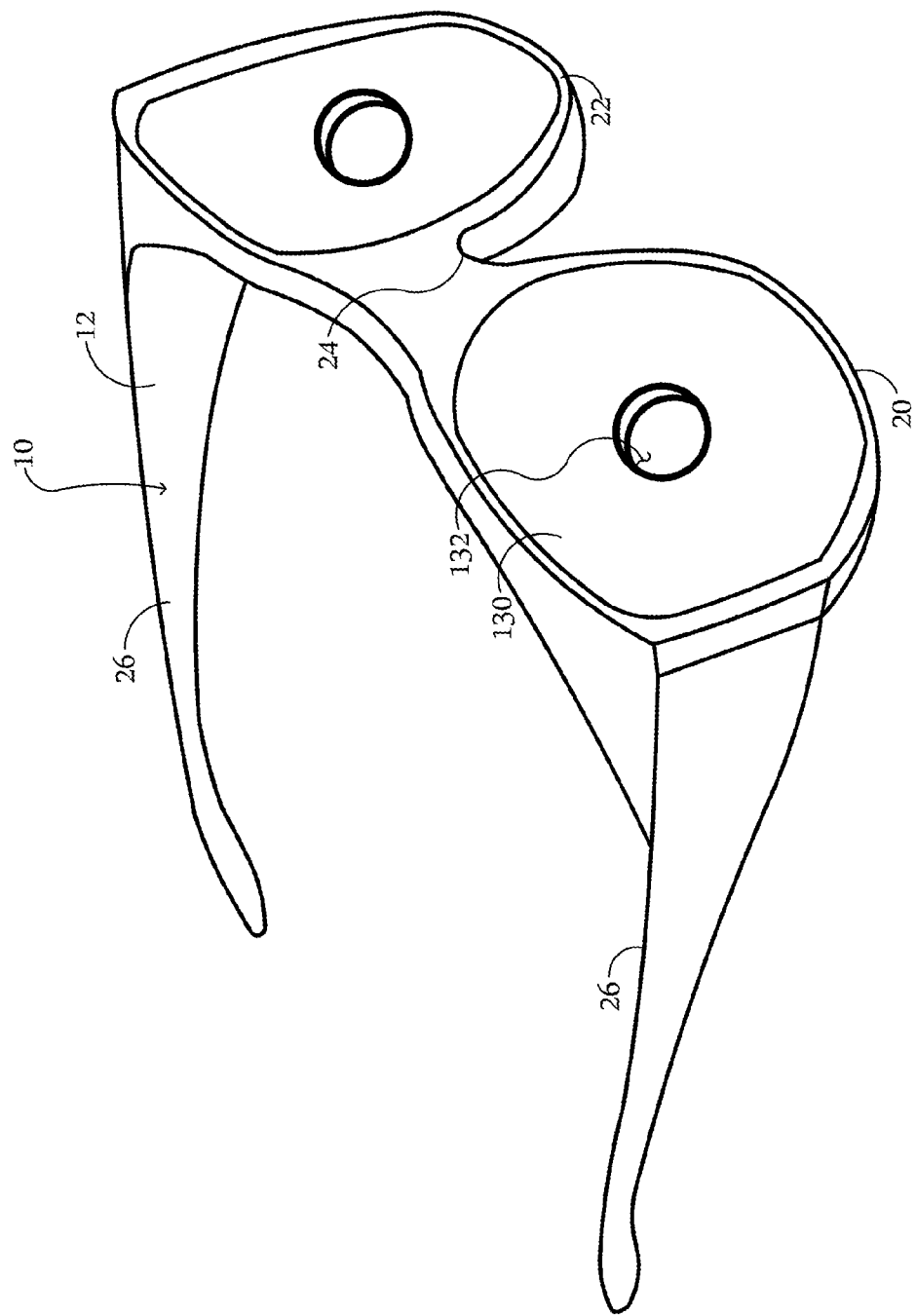
FIG. 11 is an isometric view of another embodiment.

Another embodiment, shown in FIG. 11, does not utilize the at least one guide device 14, but instead provides for at least one lens 130 having an "unobstructed aperture 132." As before, this embodiment utilizes a frame assembly 12 resembling a pair of glasses, and the same reference numbers shall be used for like elements. An "unobstructed aperture" as used herein, shall mean an aperture that provides a view free from obstructions such as, but not limited to, a threaded socket for an applicator nozzle 2 or other constructs adapted to grip, i.e. apply pressure to, a nozzle 2 such as, but not limited to, radial slots/radial fingers.

Figure 12:
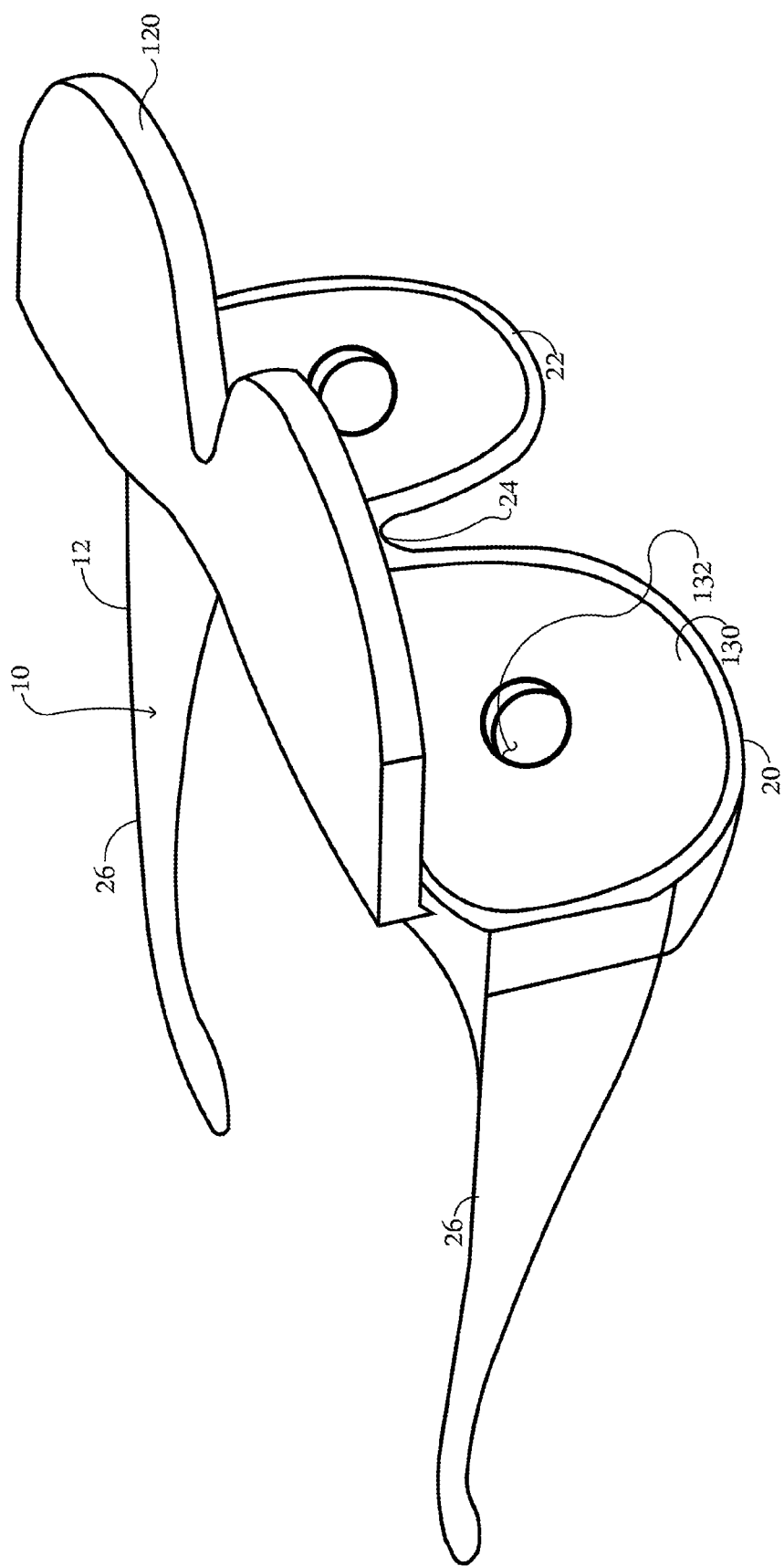
FIG. 12 is an isometric view of the embodiment in FIG. 11 and a movable lens.

As shown, the at least one lens 130 is disposed in one loop 20 of the frame assembly 12. The at least one lens 130 is transparent. The at least one lens 130 includes an unobstructed aperture 132, which is an opening free from any other constructs, e.g. a threaded socket. The unobstructed aperture 132 is, preferably, circular, thereby forming a cylindrical passage through the at least one lens 130. The longitudinal axis of the unobstructed aperture 132 is substantially normal to the surface of the at least one lens 130. The unobstructed aperture 132 is sized to accommodate a typical nozzle 2. That is, the unobstructed aperture 132, preferably, has a radius of between 0.20 in. and 0.50 in., and more preferably about 0.25 in. The unobstructed aperture 132 is disposed at a central location on the at least one lens 130. In this embodiment, the at least one lens 130 may be, and preferably is, a simple, non-corrective lens. As a non-corrective lens, the at least one lens 130 may be very thin, preferably having a thickness of between 0.04 in. and 0.07 in., and more preferably about 0.05 in. This thinness of the at least one lens 130 reduces the amount of light refracted by the unobstructed aperture 132, thereby reducing the visibility of the unobstructed aperture 132. As with the embodiment above, the frame assembly 12 having at least one lens 130 with an unobstructed aperture 132 may include at least one movable lens 120, as shown in FIG. 12. Thus, the at least one movable lens 120 may be selected from the group comprising: a corrective lens, a shaded lens, and a shaded corrective lens.

Figure 13:
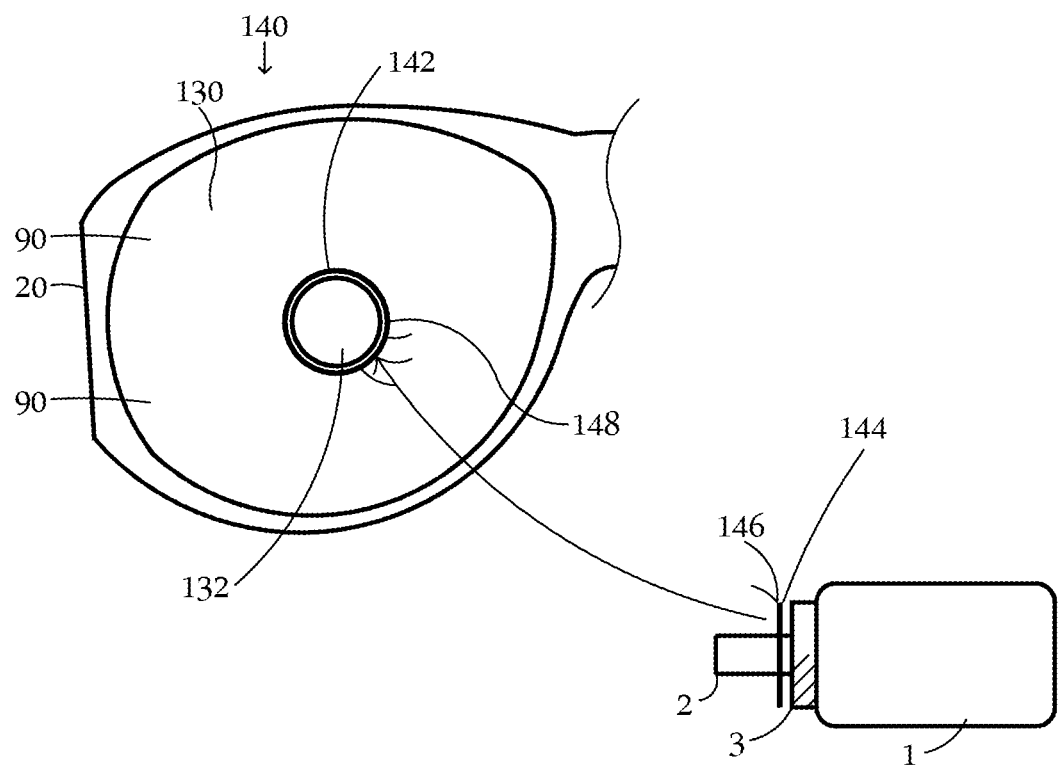
FIG. 13 is a front view of another embodiment having a magnetic material disposed about the unobstructed aperture.

In use, a user typically tilts their head back so that the unobstructed aperture 132 is disposed above their eye. The user then positions the applicator nozzle 2 in the unobstructed aperture 132 and applies the medicine. As shown in FIG. 13, however, the at least one lens 130 may include a magnetic alignment device 140. The magnetic alignment device 140 includes two magnetic elements 142, 144. A first magnetic element 142 is dispose about the unobstructed aperture 132. The second magnetic element 144 is a torus 146, i.e. a ring or a disk having a central opening, structured to be coupled to the applicator nozzle 2. The torus 146 may also include a plurality of radial slits (not shown) whereby the central portion of the torus 146 is flexible. In this configuration, the central opening may be expanded so as to fit onto applicator nozzles 2 of different sizes. At least one of the two magnetic elements 142, 144 must be magnetic. In the preferred embodiment, the first magnetic element 142 is an iron or steel ring 148, or wire, disposed about the unobstructed aperture 132 and the second magnetic element 144, i.e. the torus 146, is a magnet.

In use, the user, who may have difficulties with motor control, positions the applicator nozzle 2 adjacent the unobstructed aperture 132. As the applicator nozzle 2 is moved toward the unobstructed aperture 132, the magnetic force between the two magnetic elements 142, 144 helps align the applicator nozzle 2 with the unobstructed aperture 132 and may draw the applicator nozzle 2 into the unobstructed aperture 132.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention which is to be given the full breadth of the claims appended and any and all equivalents thereof.

What is claimed is:

1. An eye treatment apparatus comprising:
   an eyeglass frame assembly having at least one frame member structured to be disposed adjacent to at least one eye;
   at least one guide device structured to be positioned in front of at least one eye, said guide device having a guide surface structured to engage an applicator nozzle, said at least one guide device coupled to said frame assembly; and
   wherein said at least one guide device is easily accessible; and
   wherein said at least one guide device includes a stop.

2. The eye treatment apparatus of claim 1 wherein said least one guide device is structured to centrally position an applicator nozzle in front of at least one eye.

3. The eye treatment apparatus of claim 1 wherein said at least one guide device includes two guide devices, one guide device structured to be positioned in front of each of the user's eyes.

4. The eye treatment apparatus of claim 1 wherein:
   said at least one guide device includes a vertex; and
   wherein said vertex is said stop.

5. The eye treatment apparatus of claim 1 wherein:
said frame assembly includes tension members structured to be positioned in front of at least one eye;
said tension members forming a vertex; and
one said tension member being said guide surface and said vertex being a stop.

6. The eye treatment apparatus of claim 5 wherein:
said vertex is created by two tension members crossing over each other;
said two tension members forming two obtuse angles; and
wherein said obtuse angles face vertically.

7. The eye treatment apparatus of claim 1 wherein said frame assembly includes at least one loop.

8. The eye treatment apparatus of claim 1 wherein said frame assembly includes at least one partial loop.

9. The eye treatment apparatus of claim 8 wherein said guide surface extends over said partial loop.

10. The eye treatment apparatus of claim 1 wherein:
said frame assembly includes at least one transparent lens structured to be positioned in front of at least one eye; and
said at least one guide device being an opening in said lens, said opening having a guide surface.

11. The eye treatment apparatus of claim 10 wherein said lens opening is selected from the group comprising: a slot and a V-shaped cutout.

12. The eye treatment apparatus of claim 11 wherein:
said frame assembly further includes at least one movable lens, said movable lens being movably coupled to said frame assembly; and
said movable lens structured to move between two positions, a first position wherein said movable lens is disposed in front of the user's eye, and a second position, wherein said movable lens is not disposed in front of the user's eye.

13. The eye treatment apparatus of claim 12 wherein said movable lens is selected from the group comprising: a corrective lens, a shaded lens, and a shaded corrective lens.

14. The eye treatment apparatus of claim 10 wherein said lens opening is structured to centrally position an applicator nozzle in front of at least one eye.

15. The eye treatment apparatus of claim 10 wherein said frame assembly includes at least one loop.

16. The eye treatment apparatus of claim 10 wherein said frame assembly includes at least one partial loop.

17. An eye treatment apparatus comprising:
an eyeglass frame assembly having at least one frame member structured to be disposed adjacent to at least one eye; and
at least one lens having an unobstructed aperture, said unobstructed aperture disposed at a central location; and
wherein said frame assembly further includes at least one movable lens, said movable lens being movably coupled to said frame assembly; and
said movable lens structured to move between two positions, a first position wherein said movable lens is disposed in front of the user's eye, and a second position, wherein said movable lens is not disposed in front of the user's eye.

18. An eye treatment apparatus comprising:
an eyeglass frame assembly having at least one frame member structured to be disposed adjacent to at least one eye;
at least one easily accessible guide device structured to be positioned in front of at least one eye, said guide device having a guide surface structured to engage an applicator nozzle, said at least one guide device coupled to said frame assembly;
said frame assembly includes at least one transparent lens structured to be positioned in front of at least one eye;
said at least one guide device being an opening in said lens, said opening having a guide surface; and
wherein said lens opening includes a slot formed between a top and bottom portion of the lens.

* * * * *